(12) United States Patent
Gao et al.

(10) Patent No.: US 12,043,825 B2
(45) Date of Patent: Jul. 23, 2024

(54) **SOLID MEDIUM FOR *CORIOLUS VERSICOLOR*, AND PREPARATION METHOD AND USE**

(71) Applicant: Beijing University of Civil Engineering and Architecture, Beijing (CN)

(72) Inventors: Dawen Gao, Beijing (CN); Teng Tang, Beijing (CN); Hong Liang, Beijing (CN); Litao Wang, Beijing (CN)

( * ) Notice: Subject to any disclaimer, the term of this patent is extended or adjusted under 35 U.S.C. 154(b) by 0 days.

(21) Appl. No.: 17/813,977

(22) Filed: Jul. 21, 2022

(65) Prior Publication Data

US 2023/0279335 A1 Sep. 7, 2023

(30) Foreign Application Priority Data

Mar. 1, 2022 (CN) .......................... 202210192250.4

(51) Int. Cl.
*C12N 1/14* (2006.01)
(52) U.S. Cl.
CPC ............ *C12N 1/14* (2013.01); *C12N 2500/10* (2013.01); *C12N 2500/76* (2013.01)
(58) Field of Classification Search
CPC ...................................................... C12N 1/14
See application file for complete search history.

*Primary Examiner* — Suzanne M Noakes
(74) *Attorney, Agent, or Firm* — Gunn, Lee & Cave, P.C.; Robert L. McRae

(57) ABSTRACT

The present disclosure relates to the technical field of culture materials for fungi and provides a solid medium for *Coriolus versicolor*, and a preparation method and use. Bran is used as a main component in the solid medium, and has advantages in economy and environmental protection, and provides high *Coriolus versicolor* growth rate and strong contamination resistance. The solid medium avoids the tendency to contamination of current media during an experimental process, and reduces culture cost. The solid medium provides higher biomass and stronger contamination resistance than a potato dextrose agar (PDA) medium.

8 Claims, 2 Drawing Sheets

SOLID MEDIUM FOR *CORIOLUS VERSICOLOR*, AND PREPARATION METHOD AND USE

CROSS REFERENCE TO RELATED APPLICATION

This patent application claims the benefit and priority of Chinese Patent Application No. 202210192250.4, entitled Solid Medium for *Coriolus Versicolor*, And Preparation Method and Use filed on Mar. 1. 2022, the disclosure of which is incorporated by reference herein in its entirety as part of the present application.

TECHNICAL FIELD

The present disclosure belongs to the technical field of culture materials for fungi, and in particular relates to a solid medium for *Coriolus versicolor*, and a preparation method and use.

BACKGROUND ART

The "Report on the National General Survey of Soil Contamination" released in 2014 shows that the national soil environment in China is generally not optimistic. Some regions have relatively serious soil pollution, the soil environment of agricultural arable land has a worrisome quality, and the soil environment of industrial and mining wasteland also has serious problems. The soil pollution has become a non-negligible problem that threatens human health. Compared with physical and chemical remediation, biological remediation, due to outstanding advantages in environmental friendliness and economy, is the future direction of soil remediation.

*Coriolus versicolor*, classified and identified from the forest area of northeast China, belongs to the genus *Coriolus* of Polyporaceae and is a typical white-rot fungus. Laccase is a biological enzyme known to degrade polycyclic aromatic hydrocarbons, petroleum hydrocarbons, and halogenated hydrocarbons and other pollutants widely existing in the environment, and *Coriolus versicolor*, as a strain with a strong ability to secrete the laccase reported in the literature, is a potential strain for soil remediation in the future.

As a first step of soil biological remediation, it is necessary to conduct solid culture on bacteria used for remediation in the laboratory. However, the traditionally-used potato dextrose agar (PDA) solid medium generally has high cost and easy contamination during the experiment, which cannot obtain repaired strains in a short time. This will affect the subsequent preparation of microbial inoculants or crude enzyme solutions and use thereof in contaminated soil. Although it has been experimentally proven that antibiotics can be added to the solid medium to inhibit bacterial growth. However, the amount of antibiotics added is relatively strict, and excessive antibiotics will inhibit biomass, activity and enzyme production capacity of the strains. Therefore, this scheme cannot be used as the best solution to eliminate the contamination.

SUMMARY

In view of this, an objective of the present disclosure is to provide a solid medium for *Coriolus versicolor*, and a preparation method and use. The present disclosure avoids long culturing time and tendency to contamination in culturing *Coriolus versicolor* using a traditional PDA medium, reduces culture cost, and improves biomass and antibacterial ability of *Coriolus versicolor*.

To achieve the above objective, the present disclosure provides the following technical solutions.

The present disclosure provides a solid medium for *Coriolus versicolor*, including the following raw materials: bran, xylose, a trace element solution, agar, and water, where the bran and xylose have a mass ratio of 8:3 to 1:1.

Preferably, trace elements in the trace element solution may include Mg, Mn, Na, Fe, Co, Ca, Zn, Cu, K, B, and Mo.

Preferably, trace elements in the trace element solution may be provided by $MgSO_4$, $MnSO_4$, NaCl, $FeSO_4$, $CoSO_4$, $CaCl_2$, $ZnSO_4$, $CuSO_4$, $KAl(SO_4)_2$, $H_3BO_3$, and $NaMoO_4$, respectively.

Preferably, $MgSO_4$ may be provided in a form of $MgSO_4 \cdot 7H_2O$, $FeSO_4$ may be provided in a form of $FeSO_4 \cdot 7H_2O$, and $CuSO_4$ may be provided in a form of $CuSO_4 \cdot 5H_2O$.

Preferably, the trace element solution may include 3.0 g/L of $MgSO_4 \cdot 7H_2O$, 0.5 g/L, of $MnSO_4$, 1.0 g/L of NaCl, 0.1 g/L of $FeSO_4 \cdot 7H_2O$, 0.1 g/L of $CoSO_4$, 0.082 g/L of $CaCl_2$, 0.1 g/L of $ZnSO_4$, 0.01 g/L of $CuSO_4 \cdot 5H_2O$, 0.01 g/L of $KAl(SO_4)_2$, 0.01 g/L of $H_3BO_3$, and 0.01 g/L of $NaMoO_4$.

Preferably, the solid medium may include 1.36 mL to 2 mL of the trace element solution per liter of the solid medium.

The present disclosure further provides a preparation method of the solid medium, including the following steps when preparing each liter of the solid medium: mixing the bran with 500 mL of boiled water, boiling for 25 min, and filtering to collect a bran extract, and mixing the bran extract with xylose, the agar, the trace element solution, and part of water, boiling, diluting to 1 liter with water, and sterilizing and cooling to obtain the solid medium.

Preferably, the filtering may be conducted by using 9-layer gauze.

The present disclosure further provides use of the solid medium in improving a growth rate and enhancing a contamination resistance of *Coriolus versicolor*.

The present disclosure further provides a method for culturing *Coriolus versicolor*, including the following steps: inoculating a strain of *Coriolus versicolor* on the solid medium, sealing, and culturing the solid medium at 28° C.

Beneficial effects are as follows: bran is used as a main component in the solid medium, which has the advantages of being economic and environmentally friendly, and provides high *Coriolus versicolor* growth rate and strong resistance to contamination. The solid medium avoids the tendency to contamination of current media during an experimental process, and reduces culture cost. In the examples of the present disclosure, the solid medium was added to a 90 mm petri dish, and an average biomass of 0.30135 g was obtained after culturing for 7 days; while the traditional PDA medium only provided a biomass of 0.27185 g on a petri dish of the same size. Within a same time, the novel solid medium for *Coriolus versicolor* can obtain more biomass, which is beneficial to subsequent liquid fermentation of the strains to produce enzymes and solid fermentation of the strains to obtain microbial inoculants. After 2 min of air exposure, the novel solid medium for *Coriolus versicolor* showed only 40% contamination, while the PDA medium showed 100% contamination.

DETAILED DESCRIPTION OF THE EMBODIMENTS

Figure 1:
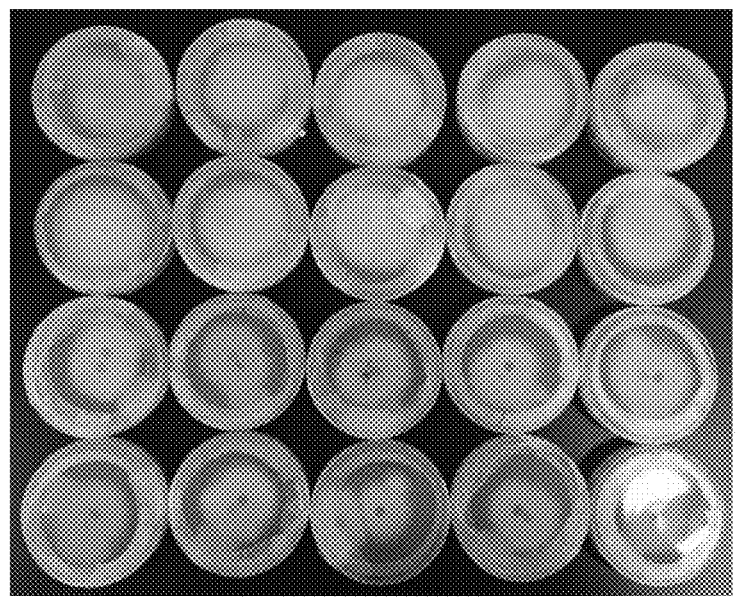
FIG. 1 shows a biomass comparison of *Coriolus versicolor* after culturing in different media for 7 days; where from top to bottom, the 1st to 2nd rows represent culturing in a solid medium for the present disclosure, and the 3rd to 4th rows represent culturing in a PDA solid medium.

The present disclosure provides a solid medium for *Coriolus versicolor*, including the following raw materials: bran, xylose, a trace element solution, agar, and water; where the bran and xylose have a mass ratio of 8:3 to 1:1.

In the present disclosure, bran is used as a main component in the solid medium, and each liter of the raw materials of the solid medium includes preferably 30 g to 40 g, more preferably 40 g of the bran. The solid medium has the advantages of being economic and environmentally friendly, and provides high *Coriolus versicolor* growth rate and strong resistance to contamination, and reduces culture cost. There is no special limitation on a source of the bran, and conventional commercially available products in the field can be used.

In the present disclosure, the solid medium includes xylose, which is an intermediate product obtained by metabolizing lignin in an original growth environment of *Coriolus versicolor*, and is used as a carbon source. Each liter of the raw materials of the solid medium includes preferably 15 g to 30 g, more preferably 30 g of xylose. There is no special limitation on a source of xylose, and conventional commercially available products in the field can be used. Each liter of the solid medium includes preferably 40 g of bran and 30 g of xylose.

In the present disclosure, the solid medium includes a trace element solution, trace elements in the trace element solution include preferably Mg, Mn, Na, Fe, Co, Ca, Zn, Cu, K, B, and Mo; and the trace elements are provided preferably by $MgSO_4$, $MnSO_4$, $NaCl$, $FeSO_4$, $CoSO_4$, $CaCl_2$, $ZnSO_4$, $CuSO_4$, $KAl(SO_4)_2$, $H_3BO_3$, and $NaMoO_4$, respectively. $MgSO_4$ is preferably $MgSO_4 \cdot 7H_2O$, $FeSO_4$ is preferably $FeSO_4 \cdot 7H_2O$, and $CoSO_4$ is preferably $CuSO_4 \cdot 5H_2O$. In an example, the trace element solution include preferably 3.0 g/L of $MgSO_4 \cdot 7H_2O$, 0.5 g/L of $MnSO_4$, 1.0 g/L of NaCl, 0.1 g/L of $FeSO_4 \cdot 7H_2O$, 0.1 g/L of $CoSO_4$, 0.082 g/L, of $CaCl_2$, 0.1 g/L of $ZnSO_4$, 0.01 g/L of $CuSO_4 \cdot 5H_2O$, 0.01 g/L of $KAl(SO_4)_2$, 0.01 g/L of $H_3BO_3$, and 0.01 g/L of $NaMoO_4$. Each liter of the solid medium includes preferably 1.36 mL to 2 mL, more preferably 1.5 ml, of the trace element solution. There is no special limitation on a source of the various trace elements, and conventional reagents in the field can he used. There is also no special limitation on a preparation method of the trace element solution, and conventional methods in the field can be used for dissolving and diluting.

In the present disclosure, the solid medium includes agar, and the agar has a final mass concentration of preferably 2% of a mass of the solid medium.

The present disclosure further provides a preparation method of the solid medium, including the following steps when preparing each liter of the solid medium: mixing the bran with 500 mL of boiled water, boiling for 25 min, and filtering to collect a bran extract; and mixing the bran extract with xylose, the agar, the trace element solution, and part of water, boiling, diluting to 1 liter with water, and sterilizing and cooling to obtain the solid medium.

In the present disclosure, the filtering is conducted using preferably 9 layers of gauze.

In the present disclosure, the sterilizing is conducted preferably at high temperature and high pressure, more preferably by autoclaving at 121° C. for 20 min. After the sterilizing, preferably a sterilized medium is evenly distributed to each plate or petri dish. In one example, 30 mL of the sterilized medium is poured into each 90 mm petri dish, followed by standing to cool the sterilized medium.

The present disclosure further provides use of the solid medium in improving a growth rate and enhancing a contamination resistance of *Coriolus versicolor*.

in the present disclosure, bran, an agricultural waste, is used as a main component in the solid medium; xylose, an intermediate product obtained by metabolizing lignin in an original Growth environment of *Coriolus versicolor*, is used as an additional carbon source, and is added with trace elements that are indispensable for biological growth; the solid medium has desirable economy and waste recyclability, short incubation time (7 d), and certain antibacterial ability. Therefore, the solid medium can be used for improving a growth rate and enhancing contamination resistance of *Coriolus versicolor*.

The present disclosure further provides a method for culturing *Coriolus versicolor*, including the following steps: inoculating a strain of *Coriolus versicolor* on the solid medium, sealing, and culturing the solid medium at 28° C. In the present disclosure, the inoculating includes preferably making a preserved medium covered with *Coriolus versicolor* into 10 mm bacterial flakes, inoculating the bacterial flakes on the solid medium, where 2 bacterial flakes can be inoculated in each petri dish; sealing a lower part of the petri dish using a sealing film; and placing the petri dish in a biological incubator, followed by conducting culture at 28° C.

By using the culturing method of the present disclosure, the biomass can reach 0.30135 g per dish after culturing for 7 days; meanwhile, the inoculating and culturing are conducted after the solid medium is placed in the air, and a bacterial infection rate is 40% after 7 days, which has a significant reduction compared with a 100% bacterial infection rate of PDA medium under the same conditions.

The solid medium for *Coriolus versicolor*, and the preparation method and the use provided by the present disclosure will be described in detail below with reference to examples, but they cannot be understood as limiting the claimed scope of the present disclosure.

Example 1 Preparation of a Solid Medium

A. Preparation of a trace element solution: 3.0 g of $MgSO_4\ 7H_2O$, 0.5 g of $MnSO_4$, 1.0 g of NaCl, 0.1 g of $FeSO_4\ 7H_2O$, 0.1 g of $CoSO_4$, 0.082 g of $CaCl_2$, 0.1 g of $ZnSO_4$, 0.01 g of $CuSO_4 \cdot 5H_2O$, 0.01 g of $KAl(SO_4)_2$, 0.01 g of $H_3BO_3$, and 0.01 g of $NaMoO_4$ were weighed by an analytical balance, dissolved in distilled water and diluted to 1,000 m/L.

B. 40 g of bran and 30 g of xylose were weighed by an analytical balance for later use.

C. The bran was added to 500 mL of boiled distilled water, boiled for 25 min, and filtered with 9 layers of gauze to obtain a bran extract.

D. After adding the distilled water appropriately, 30 g of xylose, 1.5 mL of trace elements, and agar with a final concentration of 2% (m/m) were added, and boiled.

E. After diluting to 1,000 m/L, with the distilled water, autoclaving was conducted at 121° C. for 20 min, 30 mL of a medium was poured into a 90 mm petri dish, and cooled to obtain a solid medium for *Coriolus versicolor* for later use.

Example 2 Inoculation of *Coriolus Versicolor*

1. Experimental Example

A. On a sterile operating bench, a PDA medium covered with *Coriolus versicolor* was punched into 10 mm bacterial flakes using a sterile punch.

B. The bacterial flakes were inoculated on the solid medium prepared in Example 1, where each solid medium was inoculated with 2 bacterial -flakes.

C. A lower part of the petri dish was sealed using a sealing film.

D. The petri dish with the solid medium was placed in a biological incubator, followed by conducting culture at 28° C.

2. Comparative Example 46 g of the PDA medium (purchased from Qingdao Hope Bio-Technology Co., Ltd.) was weighed to prepare a solid medium, and other operations were the same as those in the Experimental Example; where 4 duplicates were set up.

The biomass was measured after 7 days in a biochemical incubator, and the results were shown in FIG. 1. The Experimental Example has biomass of 0.30135 g/dish, while the Comparative Example has biomass of only 0.27185 g/dish. That is to say, within a same time, using the solid medium of the present disclosure gave a higher growth rate than using the PDA medium, and a larger amount of biomass was obtained.

3. Enzyme activity assay

The *Coriolus versicolor* strains cultured on each medium were separately transferred to a liquid medium according to Yao Meng's method to conduct the enzyme activity assay (Yao Meng. Preparation method of white-rot fungus-based compound microbial inoculants and research on petroleum-contaminated soil remediation [D]. Northeast Forestry University, 2012).

Figure 2:
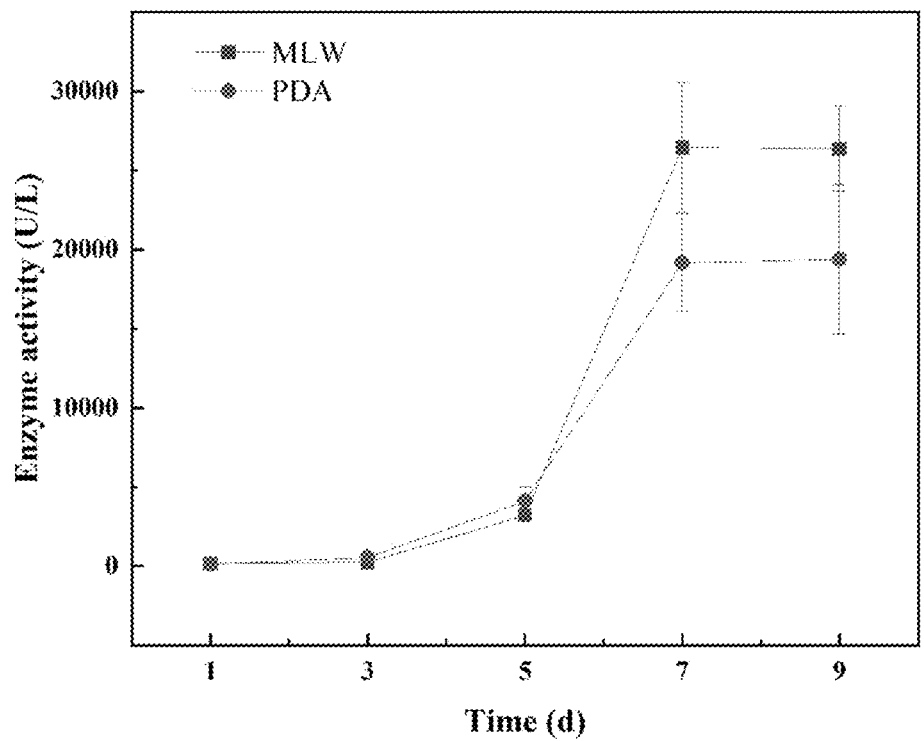
FIG. 2 shows determination of laccase activity of *Coriolus versicolor* after culturing in different media for 7 days.

The experimental results are shown in FIG. 2. The enzyme activity of the solid medium of the present disclosure transferred to the liquid medium (with a highest average enzyme activity of 26445.2818 U/L) is higher than that of the PDA medium transferred to the liquid medium in the same period (with a highest average enzyme activity of 19394.3703 U/L).

Example 3 Comparison of a contamination resistance

1. Experimental group: the solid medium prepared in Example 1 was exposed to the air for 2 min, placed in a biochemical incubator at 28° C. for 7 days, and contamination of the medium was observed; where there were 5 duplicates.

2. Control group: 46 g of PDA (purchased from Qingdao Hope Bio-Technology Co., Ltd.) was weighed to prepare a solid medium, autoclaved at 121° C. for 20 min, exposed to air for 2 min, and placed in a biochemical incubator at 28° C. for 7 d, and contamination of the medium was observed; where there were 5 duplicates.

Figure 3:
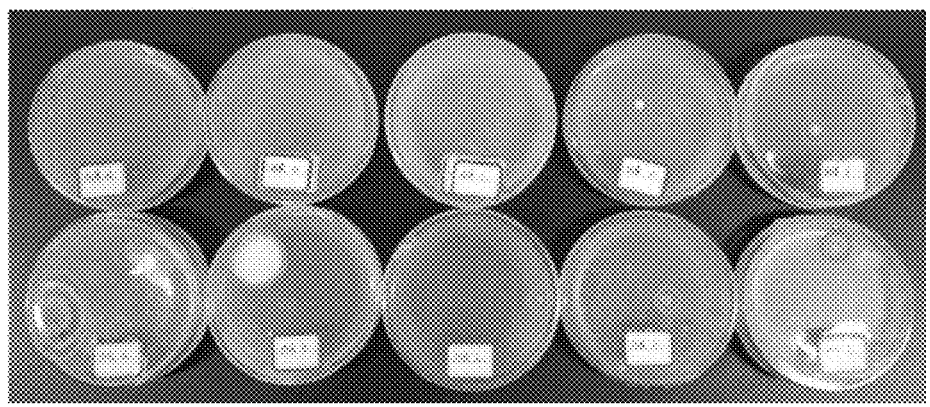
FIG. 3 shows a contamination resistance test result of the solid medium of the present disclosure.

The results are shown in FIG. 3. 40% bacterial infection rate occurred in the experimental group, while 100% bacterial infection rate occurred in the control group, indicating that the solid medium of the present disclosure has obvious advantages in contamination resistance compared with the existing PDA medium.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A solid medium for Coriolus versicolor, comprising the following raw materials: bran, xylose, a trace element solution, agar, and water; wherein the bran and xylose have a mass ratio of 8:3 to 1:1;

wherein trace elements in the trace element solution comprise Mg, Mn, Na, Fe, Co, Ca, Zn, Cu, K, B, and Mo, and the trace elements in the trace element solution are provided by $MgSO_4$, $MnSO_4$, $NaCl$, $FeSO_4$, $CoSO_4$, $CaCl_2$, $ZnSO_4$, $CuSO_4$, $KAl(SO_4)_2$, $H_3BO_3$, and $NaMoO_4$.

2. The solid medium according to claim 1, wherein $MgSO_4$ is provided in a form of $MgSO_4 \cdot 7H_2O$, $FeSO_4$ is provided in a form of $FeSO_4 \cdot 7H_2O$, and $CuSO_4$ is provided in a form of $CuSO_4 \cdot 5H_2O$.

3. The solid medium according to claim 2, wherein the trace element solution comprises 3.0 g/L of $MgSO_4 \cdot 7H_2O$, 0.5 g/L of $MnSO_4$, 1.0 g/L of $NaCl$, 0.1 g/L of $FeSO_4 \cdot 7H_2O$, 0.1 g/L of $CoSO_4$, 0.082 g/L of $CaCl_2$, 0.1 g/L of $ZnSO_4$, 0.01 g/L of $CuSO_4 \cdot 5H_2O$, 0.01 g/L of $KAl(SO_4)_2$, 0.01 g/L of $H_3BO_3$, and 0.01 g/L of $NaMoO_4$.

4. The solid medium according to claim 1, wherein each liter of the solid medium comprises 1.36 mL to 2 mL of the trace element solution.

5. The solid medium according to claim 3, wherein each liter of the solid medium comprises 1.36 mL to 2 mL of the trace element solution.

6. A preparation method of the solid medium according to claim 1, comprising the following steps when preparing each liter of the solid medium: mixing the bran with 500 mL of boiled water, boiling for 25 min, and filtering to collect a bran extract; and mixing the bran extract with xylose, the agar, the trace element solution, and water, boiling, diluting to 1 liter with water, and sterilizing and cooling to obtain the solid medium.

7. The preparation method according to claim 6, wherein the filtering is conducted by using a 9-layer gauze.

8. A method for culturing Coriolus versicolor, comprising the following steps: inoculating a strain of the Coriolus versicolor on the solid medium according to claim 1, sealing, and culturing at 28° C.

* * * * *